(12) United States Patent
Powers

(10) Patent No.: US 6,979,757 B2
(45) Date of Patent: Dec. 27, 2005

(54) OLEFIN PRODUCTION UTILIZING WHOLE CRUDE OIL AND MILD CONTROLLED CAVITATION ASSISTED CRACKING

(75) Inventor: Donald H. Powers, Pearland, TX (US)

(73) Assignee: Equistar Chemicals, LP, Houston, TX (US)

( * ) Notice: Subject to any disclaimer, the term of this patent is extended or adjusted under 35 U.S.C. 154(b) by 307 days.

(21) Appl. No.: 10/616,839

(22) Filed: Jul. 10, 2003

(65) Prior Publication Data

US 2005/0010075 A1    Jan. 13, 2005

(51) Int. Cl.[7] .............................. C07C 4/04; C10G 9/36
(52) U.S. Cl. ........................ 585/648; 585/652; 208/130
(58) Field of Search .............................. 585/648, 652; 208/130

(56) References Cited

U.S. PATENT DOCUMENTS

| | | | | |
|---|---|---|---|---|
| 3,617,493 A | * | 11/1971 | Wirth et al. | 208/80 |
| 5,188,090 A | | 2/1993 | Griggs | 126/247 |
| 5,492,654 A | | 2/1996 | Kozjuk et al. | 261/76 |
| 5,810,052 A | | 9/1998 | Kozyuk | 138/37 |
| 5,817,226 A | | 10/1998 | Lenglet | 208/130 |
| 6,743,961 B2 | | 6/2004 | Powers | 585/648 |

OTHER PUBLICATIONS

*Ulman's Encyclopedia of Industrial Chemistry*, 5th Edition, vol. A10, VCH Publishing, 1988, ISBN: 0895731606.

* cited by examiner

*Primary Examiner*—Thuan D Dang
(74) *Attorney, Agent, or Firm*—Roderick W. MacDonald

(57) ABSTRACT

A method for utilizing whole crude oil as a feedstock for the pyrolysis furnace of an olefin production plant wherein the feedstock after preheating is subjected to mild thermal cracking assisted with controlled cavitation conditions until substantially vaporized, the vapors being subjected to severe cracking in the radiant section of the furnace.

16 Claims, 1 Drawing Sheet

OLEFIN PRODUCTION UTILIZING WHOLE CRUDE OIL AND MILD CONTROLLED CAVITATION ASSISTED CRACKING

BACKGROUND OF INVENTION

1. Field of Invention

This invention relates to the formation of olefins by thermal cracking of whole crude oil. More particularly, this invention relates to utilizing whole crude oil as a feedstock for an olefin production plant that employs a hydrocarbon cracking process such as steam cracking in a pyrolysis furnace.

2. Description of the Prior Art

Thermal cracking of hydrocarbons is a petrochemical process that is widely used to produce olefins such as ethylene, propylene, butenes, butadiene, and aromatics such as benzene, toluene, and xylenes.

Basically, a hydrocarbon feedstock such as naphtha, gas oil or other fractions of whole crude oil that are produced by distilling or otherwise fractionating whole crude oil, is mixed with steam which serves as a diluent to keep the hydrocarbon molecules separated. The steam/hydrocarbon mixture is preheated to from about 900° F. to about 1,000° F., and then enters the reaction zone where it is very quickly heated to a severe hydrocarbon cracking temperature in the range of from about 1,450° F. to about 1,550° F.

This process is carried out in a pyrolysis furnace (steam cracker) at pressures in the reaction zone ranging from about 10 to about 30 psig. Pyrolysis furnaces have internally thereof a convection section and a radiant section. Preheating is accomplished in the convection section, while severe cracking occurs in the radiant section.

After severe cracking, the effluent from the pyrolysis furnace contains gaseous hydrocarbons of great variety, e.g., from one to thirty-five carbon atoms per molecule. These gaseous hydrocarbons can be saturated, monounsaturated, and polyunsaturated, and can be aliphatic and/or aromatic. The cracked gas also contains significant amounts of molecular hydrogen (hydrogen).

Thus, conventional steam cracking, as carried out in a commercial olefin production plant, employs a fraction of whole crude and totally vaporizes that fraction while thermally cracking same. The cracked product can contain, for example, about 1 weight percent (wt. %) hydrogen, about 10 wt. % methane, about 25 wt. % ethylene, and about 17 wt. % propylene, all wt. % being based on the total weight of said product, with the remainder consisting mostly of other hydrocarbon molecules having from 4 to 35 carbon atoms per molecule.

The cracked product is then further processed in the olefin production plant to produce, as products of the plant, various separate individual streams of high purity such as hydrogen, ethylene, propylene, mixed hydrocarbons having four carbon atoms per molecule, and pyrolysis gasoline. Each separate individual stream aforesaid is a valuable commercial product in its own right. Thus, an olefin production plant currently takes a part (fraction) of a whole crude stream and generates a plurality of separate, valuable products therefrom.

The starting feedstock for a conventional olefin production plant, as described above, has been subjected to substantial, expensive processing before it reaches that plant. Normally, whole crude is distilled or otherwise fractionated into a plurality of parts (fractions) such as gasoline, kerosene, naphtha, gas oil (vacuum or atmospheric) and the like, including a high boiling residuum. Thereafter any of these fractions, other than the residuum, could be passed to an olefin production plant as the feedstock for that plant.

It would be desirable to be able to forego the capital and operating cost of a refinery distillation unit (whole crude processing unit) that processes crude oil to generate a crude oil fraction that serves as feedstock for conventional olefin producing plants. However, the prior art teaches away from even hydrocarbon cuts (fractions) that have too broad a boiling range distribution. For example, see U.S. Pat. No. 5,817,226 to Lenglet.

SUMMARY OF THE INVENTION

In accordance with this invention there is provided a process for utilizing whole crude oil as the feedstock for an olefin producing plant with neither inadequate cracking of light fractions nor excessive cracking of heavy fractions.

Pursuant to this invention, whole crude oil is preheated, as in a conventional olefin production plant (olefin plant), to produce a mixture of hydrocarbon vapor and liquid from the crude oil feedstock with little or no coke formation. The vaporous hydrocarbon is then separated from the liquid, and the vapor passed on to a severe cracking operation. The liquid hydrocarbon remaining is subjected to mild thermal cracking that employs controlled cavitation conditions at from about 800° F. to about 1,300° F. until it is essentially all vaporized and then passed on to the severe cracking operation. Any residuum that will not crack and/or vaporize under the aforesaid mild catalytic cracking conditions remains trapped in that mild cracking operation.

DESCRIPTION OF THE DRAWING

The sole FIGURE shows one embodiment of this invention in use in conjunction with a conventional olefin plant pyrolysis furnace.

DETAILED DESCRIPTION OF THE INVENTION

Figure 1:
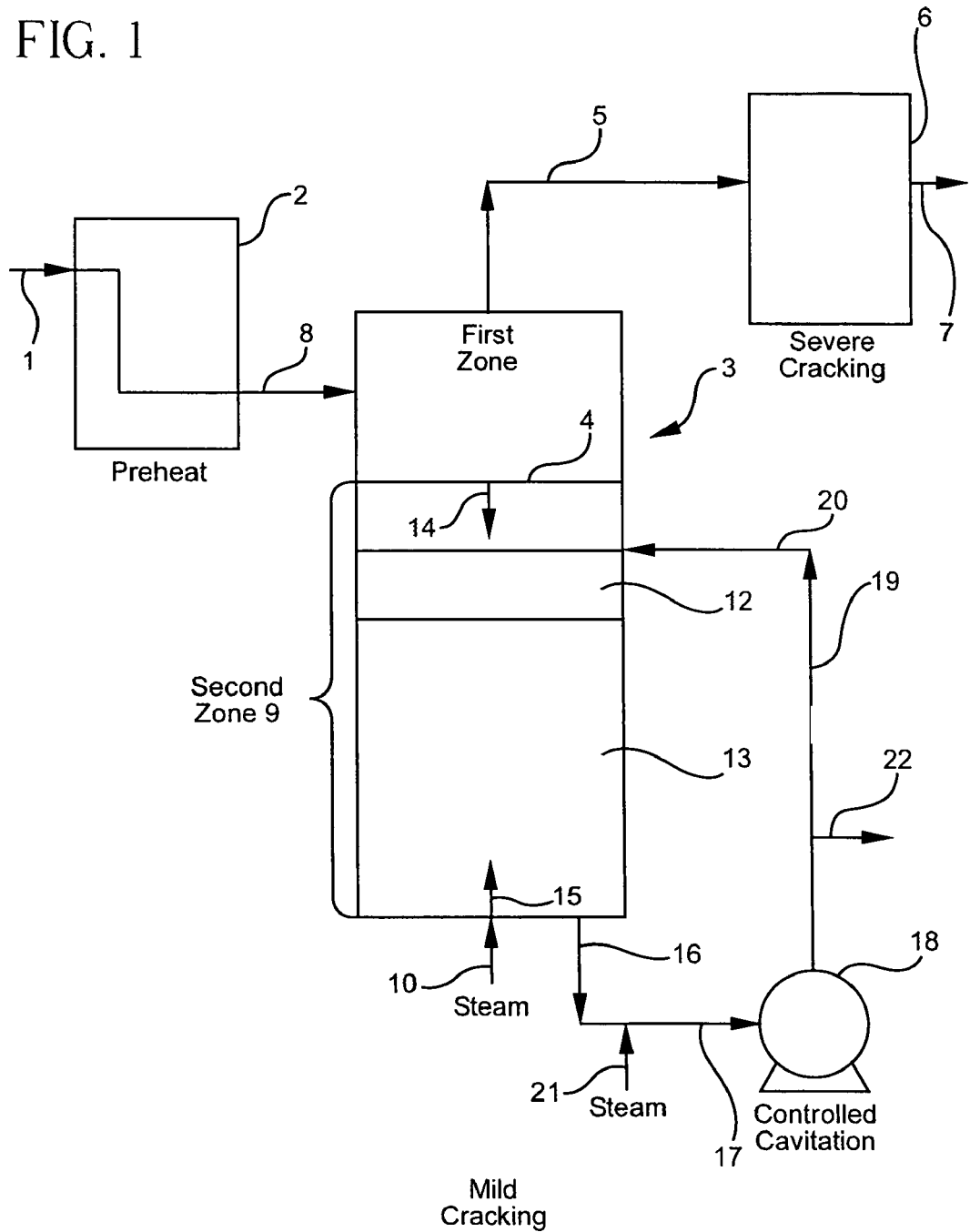

The term "whole crude oil" as used in this invention means crude oil as it issues from a wellhead except for any treatment such crude oil may receive to render it acceptable for transport to a crude oil refinery and/or conventional distillation in such a refinery. This treatment would include such steps as desalting. It is crude oil suitable for distillation or other fractionation in a refinery, but which has not undergone any such distillation or fractionation. It could include, but does not necessarily always include, non-boiling entities such as asphaltenes or tar. As such, it is difficult if not impossible to provide a boiling range for whole crude oil. Accordingly, the whole crude oil used as an initial feed for an olefin plant pursuant to this invention could be one or more crude oils straight from an oil field pipeline and/or conventional crude oil storage facility, as availability dictates, without any prior fractionation thereof.

The terms "hydrocarbon" and "hydrocarbons" as used in this invention do not mean materials strictly or only containing hydrogen atoms and carbon atoms. Such terms mean materials that are hydro carbonaceous in nature in that they primarily or essentially are composed of hydrogen and carbon atoms, but can contain other elements such as oxygen, sulfur, nitrogen, metals, inorganic salts, asphaltenes, and the like, even in significant amounts.

The terms "gas" or "gases" as used in this invention mean one or more gases in an essentially vaporous state, for example, steam alone, hydrogen alone, a mixture of steam and hydrogen, and the like.

An olefin producing plant useful with this invention would include a pyrolysis furnace for initially receiving and cracking the whole crude oil feed.

Pyrolysis furnaces for steam cracking of hydrocarbons heat by means of convection and radiation, and comprise a series of preheating, circulation, and cracking tubes, usually bundles of such tubes, for preheating, transporting, and cracking the hydrocarbon feed. The high cracking heat is supplied by burners disposed in the radiant section (sometimes called "radiation section") of the furnace. The waste gas from these burners is circulated through the convection section of the furnace to provide the heat necessary for preheating the incoming hydrocarbon feed. The convection and radiant sections of the furnace are joined at the "crossover," and the tubes referred to hereinabove carry the hydrocarbon feed from the interior of one section to the interior of the next.

Cracking furnaces are designed for rapid heating in the radiant section starting at the radiant tube (coil) inlet where reaction velocity constants are low because of low temperature. Most of the heat transferred simply raises the hydrocarbons from the inlet temperature to the reaction temperature. In the middle of the coil, the rate of temperature rise is lower but the cracking rates are appreciable. At the coil outlet, the rate of temperature rise increases somewhat but not as rapidly as at the inlet. The rate of disappearance of the reactant is the product of its reaction velocity constant times its localized concentration. At the end of the coil reactant, concentration is low and additional cracking can be obtained by increasing the process gas temperature.

Steam dilution of the feed hydrocarbon lowers the hydrocarbon partial pressure, enhances olefin formation, and reduces any tendency toward coke formation in the radiant tubes.

Cracking (pyrolysis) furnaces typically have rectangular fireboxes with upright tubes centrally located between radiant refractory walls. The tubes are supported from their top.

Firing of the radiant section is accomplished with wall or floor mounted burners or a combination of both using gaseous or combined gaseous/liquid fuels. Fireboxes are typically under slight negative pressure, most often with upward flow of flue gas. Flue gas flow into the convection section is established by at least one of natural draft or induced draft fans.

Radiant coils are usually hung in a single plane down the center of the fire box. They can be nested in a single plane or placed parallel in a staggered, double-row tube arrangement. Heat transfer from the burners to the radiant tubes occurs largely by radiation, hence the thermo "radiant section," where the hydrocarbons are heated to from about 1,450° F. to about 1,550° F. and thereby subjected to severe cracking.

The radiant coil is, therefore, a fired tubular chemical reactor. Hydrocarbon feed to the furnace is preheated to from about 900° F. to about 1,000° F. in the convection section by convectional heating from the flue gas from the radiant section, steam dilution of the feed in the convection section, or the like. After preheating, in a conventional commercial furnace, the feed is ready for entry into the radiant section.

In a typical furnace, the convection section can contain multiple zones. For example, the feed can be initially preheated in a first upper zone, boiler feed water heated in a second zone, mixed feed and steam heated in a third zone, steam superheated in a fourth zone, and the final feed/steam mixture preheated to completion in the bottom, fifth zone.

The number of zones and their functions can vary considerably. Thus, pyrolysis furnaces can be complex and variable structures.

The cracked gaseous hydrocarbons leaving the radiant section are rapidly reduced in temperature to prevent destruction of the cracking pattern. Cooling of the cracked gases before further processing of same downstream in the olefin production plant recovers a large amount of energy as high pressure steam for re-use in the furnace and/or olefin plant. This is often accomplished with the use of transfer-line exchangers that are well known in the art.

Radiant coil designers strive for short residence time, high temperature and low hydrocarbon partial pressure. Coil lengths and diameters are determined by the feed rate per coil, coil metallurgy in respect of temperature capability, and the rate of coke deposition in the coil. Coils range from a single, small diameter tube with low feed rate and many tube coils per furnace to long, large-diameter tubes with high feed rate and fewer coils per furnace. Longer coils can consist of lengths of tubing connected with u-turn bends. Various combinations of tubes can be employed. For example, four narrow tubes in parallel can feed two larger diameter tubes, also in parallel, which then feed two still larger tubes connected in series. Accordingly, coil lengths, diameters, and arrangements in series and/or parallel flow can vary widely from furnace to furnace. Furnaces, because of proprietary features in their design, are often referred to by way of their manufacturer. This invention is applicable to any pyrolysis furnace, including, but not limited to, those manufactured by Lummus, M. W. Kellog & Co., Mitsubishi, Stone & Webster Engineering Corp., KTI Corp., Linde-Selas, and the like.

Downstream processing of the cracked hydrocarbons issuing from the furnace varies considerably, and particularly based on whether the initial hydrocarbon feed was a gas or a liquid. Since this invention only uses as a feed whole crude oil which is a liquid, downstream processing herein will be described for a liquid fed olefin plant. Downstream processing of cracked gaseous hydrocarbons from liquid feedstock, naphtha through gas oil for the prior art, and whole crude oil for this invention, is more complex than for gaseous feedstock because of the heavier hydrocarbon components present in the feedstock.

With a liquid hydrocarbon feedstock downstream processing, although it can vary from plant to plant, typically employs an oil quench of the furnace effluent after heat exchange of same in, for example, a transfer-line exchanger as aforesaid. Thereafter, the cracked hydrocarbon stream is subjected to primary fractionation to remove heavy liquids such as fuel oil, followed by compression of uncondensed hydrocarbons, and acid gas and water removal therefrom. Various desired products are then individually separated, e.g., ethylene, propylene, a mixture of hydrocarbons having four carbon atoms per molecule, pyrolysis gasoline, and a high purity hydrogen stream.

More detailed information in respect of pyrolysis furnaces and their construction and operation and the cracking process can be found in Ulman's Encyclopedia of Industrial Chemistry, $5^{th}$ Edition, Vol. A10, VCH Publishing, 1988, ISBN: 0895731606.

In accordance with this invention, a process is provided which utilizes whole crude oil liquid as the primary (initial) feedstock for the olefin plant pyrolysis furnace. This is part of the novel features of this invention. By so doing, this invention eliminates the need for costly distillation of the whole crude oil into various fractions, e.g., from naphtha to gas oils, to serve as the primary feedstock for a furnace as is done by the prior art as described hereinabove.

As alluded to above, using a liquid hydrocarbon primary feedstock is more complex than using a gaseous hydrocarbon primary feedstock because of the heavier components that are present in the liquid that are not present in the gas. This is much more so the case when using whole crude oil as a primary feedstock as opposed to using liquid naphtha or gas oils as the primary feed. With whole crude oil there are more hydrocarbon components present that are normally liquids and whose natural thermodynamic tendency is to stay in that state. Liquid feeds require thermal energy to heat the liquid to its vaporization temperature, which can be quite high for heavier components, plus the latent heat of vaporization for such components.

As mentioned above, the preheated hydrocarbon stream passed to the radiant section is required to be in the gaseous state for cracking purposes, and therein lays the challenge for using whole crude oil as a primary feed to a furnace. It is also highly desirable to keep the aforesaid heavier components out of the radiation section and even the higher temperature portions of the convection section, because if they contact the inside wall of the radiant coil, they can cause the formation of undesired coke in that coil. By this invention, even though whole crude oil is used as a primary feed, the production of excessive amounts of coke are avoided. This is contrary to the prior art which teaches that feeding whole crude oil directly to a conventional steam furnace is not feasible.

By this invention, the foregoing problems with using whole crude oil as a primary feed to a furnace are avoided, and complete vaporization of the hydrocarbon stream that is passed into the radiant section of the furnace is achieved by employing a special and unique, in furnace operation, combination of a vaporization/mild cracking process unit (device) coupled with a controlled cavitation unit (device) both of which operate on the preheated whole crude oil before it enters (upstream on the radiant section of the furnace. The combination of a vaporization/mild cracking step and a controlled cavitation cracking step (operation) of this invention is a self-contained facility that operates independently of the convection and radiant sections, and can be employed as (1) an integral section of the furnace, e.g., the mild cracking section is inside the furnace in or near the convection section but upstream of the radiant section while the cavitation unit is outside the furnace and/or (2) both the mild cracking section and the cavitation unit are outside the furnace itself but in fluid communication with said furnace. When employed outside the furnace, whole crude oil primary feed is preheated in the convection section of the furnace, passed out of the convection section and the furnace to a standalone vaporization/mild cracking and controlled cavitation facility. The vaporous hydrocarbon product of this standalone facility is then passed back into the furnace to enter the radiant section thereof. Preheating can be carried out other than in the convection section of the furnace if desired or in any combination inside and/or outside the furnace and still be within the scope of this invention.

The combined vaporization/mild cracking and controlled cavitation operation of this invention receives the whole crude oil primary feed that has been preheated, for example, to from about 500° F. to about 750° F., preferably from about 550° F. to about 650° F., and heats it to from about 800° F. to about 1,300° F. to achieve mild thermal cracking of at least part of the primary feed that remains in the liquid state. This is a lower temperature range for preheated primary feed than is normally the case for primary feed that exits the preheat section of a conventional cracker and is part of the novel features of this invention. This lower preheat temperature range helps avoid fouling and coke production in the preheat section when operated in accordance with this invention. Such preheating preferably, though not necessarily, takes place in the convection section of the same furnace for which such whole crude is the primary feed.

The first zone in the vaporization/mild cracking operation step of this invention is entrainment separation wherein vaporous hydrocarbons and other gases in the preheated feed stream are separated from those components that remain liquid after preheating. The aforesaid gases are removed from the vaporization/mild cracking section and passed on to the radiant section of the furnace.

Entrainment separation in said first, e.g., upper, zone knocks out liquid in any conventional manner, numerous ways and means of which are well known and obvious in the art. Suitable devices for liquid entrainment separation include conventional distillation tower packing such as packing rings, conventional cyclone separators, schoepentoeters, vane droplet separators, and the like.

Liquid droplets separated from the vapors move, e.g., fall, downwardly, into a second, e.g., lower, zone wherein the droplets meet oncoming, e.g., rising, steam and/or hydrogen. These droplets, absent the removed gases, receive the full impact of the oncoming steam's and hydrogen's thermal energy and diluting effect.

This second zone carries in all or a portion thereof one or more distillation tower packing materials for promoting intimate mixing of liquid and vapor in the second zone.

As the liquid hydrocarbon droplets fall, they are vaporized by the high energy steam and or hydrogen. This enables the droplets that are more difficult to vaporize to continue to fall and be subjected to higher and higher steam/hydrogen to oil (liquid hydrocarbon) ratios and temperatures to enable them to be vaporized by both the energy of the steam and/or hydrogen and the decreased liquid hydrocarbon partial pressure with increased steam/hydrogen partial pressure (steam/hydrogen dilution). In addition, the steam/hydrogen may also provide energy for mild thermal cracking to reduce the molecular weight of various materials in the droplets thereby enabling them to be vaporized. For certain light whole crude oils used as primary feed in this invention, essentially only vaporization occurs with little, if any, mild cracking. However, with other heavier whole crude oils, the heavier hydrocarbon components therein resist vaporization and move in their liquid state toward the hot steam/hydrogen entering the unit until they encounter sufficiently hot steam/hydrogen and/or sufficient steam/hydrogen dilution to cause mild thermal cracking of at least a part thereof which is then followed by vaporization of the lighter molecular weight products of the mild cracking.

Hydrogen, with or without steam, aids in the vaporization and/or mild thermal cracking processes of this invention, In addition, the use of hydrogen can help to reduce, if not prevent, coke and/or polymer formation during the operation of the device of this invention. Any amount of hydrogen can be employed that is effective at least to reduce fouling, e.g., coke and/or polymer or other solid formation, the maximum amount being dictated primarily by the economics of each application rather than a functional maximum. The hydrogen can be essentially pure or admixed with other gases such as nitrogen, steam and the like. The hydrogen can be introduced at ambient temperature and/or pressure, or can be preheated into the preheat temperature and pressure set forth hereinafter.

The cavitation component of this invention applies controlled cavitation conditions to at least part of the hydro carbonaceous liquid remaining in the vaporization/mild thermal cracking section of the combination vaporization/mild thermal cracking and controlled cavitation facility of this invention.

The controlled cavitation conditions of this invention form by mechanical means a plurality of cavitation bubbles in the hydro carbonaceous liquid present in the controlled cavitation device. These bubbles then implode thereby converting into heat the mechanical energy that went into making the bubbles in the first place. The cavitation conditions are controlled so that the heat generated by the imploding bubbles (localized areas) is sufficient to thermally mildly crack suitable hydrocarbons at or near the location of the imploding bubbles (microreactors).

By this invention, and contrary to the prior art, the bulk or whole of the liquid is not heated in its entirety to effect the desired thermal cracking. Instead, the bulk of the liquid stays at a significantly lower temperature than is necessary to cause thermal cracking, thereby minimizing the potential for polymer fouling and by-product contamination. Further, the cracking heat in this component of the invention is produced internally of the liquid, i.e., the liquid does not contact heated equipment surfaces and, therefore, unwanted polymer does not readily form, thereby minimizing, if not eliminating, both frequent costly equipment clean up and by-product streams that, due to their polymer content, must be downgraded, e.g., to fuel oil.

The cavitation conditions useful in this invention can be produced by employing known cavitation devices, see U.S. Pat. No. 5,492,654 to Kozjuk et. al. and U.S. Pat. No. 5,810,052 to Kozyuk. Cavitation devices useful in this invention produce a free disperse system using the well-known cavitation effect. Cavitation generators, due to the implosion of numerous bubbles mechanically formed in the interior of the body of fluid and/or liquid (fluid) being subjected to cavitation, imparts heat to such body of fluid without the use of heated metal surfaces. With prior art cracking processes all the heat is transferred into a cooler liquid through the use of a significantly hotter metal surface. As explained above, this promotes polymer fouling. Also, the temperature differential between the hot metal surface and the cooler fluid can force certain impurities in the fluid, if present, to migrate to the hot metal surface and build up on that surface along with undesired polymer. With cavitation generators, no hot heat transfer surfaces are employed. The metal surfaces in cavitation systems can be even cooler than the fluid being processed. The heat used for cracking is formed in the interior of the fluid being processed due to the myriad of bubble dispersed therein. Thus, the heat is formed where it is needed, throughout the body of the fluid.

Accordingly, cracking heat is formed throughout the body or bulk of the fluid being processed without heating the entirety of that body to the cracking temperature. Thermal cracking is a first order chemical reaction, and, therefore, does not require a concentration of two separate molecules to proceed. Therefore, the mild thermal cracking of this component of the invention proceeds readily without heating the entire body of liquid to the required cracking temperature. Thus, the bulk of the body stays cooler. This minimizes second order chemical reactions that do require a concentration of two separate molecules at a reaction temperature to proceed.

Thus, the controlled cavitation aspect of this invention promotes cracking, but at the same time minimizes both the formation of compounds, and polymer fouling.

Cavitation in a body of fluid can be controlled in a manner such that it can be applied to heat the fluid to obtain mild cracking of a variety of hydrocarbon molecules. Cavitation generators designed to create microscopic cavitation bubbles are commercially available. Such generators employ mechanical forces such as spinning discs that contain numerous cavities in a tightly enclosed area to convert mechanical energy into microscopic bubbles within the fluid being processed. These microscopic bubbles then promptly imploded and release shock waves into the fluid. This converts mechanical energy that went into forming the bubbles into heat in the interior of the fluid without the use of heated metal surfaces that heat the entirety of the fluid. Thus, the heat necessary for effecting the desired mild thermal cracking is provided, by way of this invention, internally of the hydrocarbon liquid and dispersed in localized micro volumes of that liquid where each of the bubbles implodes. The cavitational forces created are capable of breaking down large gas bubbles into microscopic bubbles, and breaking down the Van der Waals attraction between liquid molecules.

The controlled cavitational conditions useful in this invention will vary widely due to the wide variety of hydrocarbons available in the crude oil feed used in this invention, and will be readily determinable by one skilled in the art once the feed to be cracked is identified. A degree of cavitation of at least 0.1 can be employed. Cavitation conditions that provide heat from imploded bubbles sufficient to achieve, in the location of this imploded bubble, a cracking temperature of at least about 800° F. at a pressure of from about atmospheric to about 30 psig can be used, with a temperature range of from about 800° F. to about 1,300° F. also being useful.

Controlled cavitation systems that are currently employed commercially in black liquor oxidation and heating, boiler feed mixing systems, various pulp and paper applications, and the like can be employed in this invention. The physical size of and absence of a flame source in such cavitational devices allows them to be added to existing facilities, e.g., as a pump around or feed for an existing device, without taking up large amounts of ground space. Cavitational devices useful in this invention can be operated in a batch mode. However, yet another advantage of this invention is that cavitation devices can also be operated in a semi-continuous or continuous mode and the desired cracking still achieved.

The sole Figure shows one embodiment of the application of the process of this invention. The Figure is very diagrammatic for sake of simplicity and brevity since, as discussed above, actual furnaces are complex structures. In the Figure there is shown primary feed stream 1 entering preheat section 2. Feed 1 may be mixed with diluting steam (not shown) for reasons described hereinabove before it enters section 2 and/or interiorly of section 2. Section 2 is the preheat section of a furnace, but this is not a part of the operation of this invention. Feed 1 passes through section 2 and when heated into the desired temperature range aforesaid leaves section 2 by way of line 8. In a conventional olefin plant, the preheated feed would pass from section 2, e.g., the convection section of the furnace, into the radiant section 6 of the furnace. However, pursuant to this invention, the preheated feed passes instead by way of line 8, at a temperature of from about 500° F. to about 750° F., into section 3 and upper first zone 4 wherein the gaseous components are separated from the still liquid components.

Section 3 is a vaporization/mild thermal cracking unit that is one component of the novel features of this invention.

Section 3 is not found in conjunction with conventional cracking furnaces. The gases are removed by way of line 5 and passed into the interior of radiant coils in radiant section 6 of a furnace, preferably the same furnace of which section 2 is the convection section thereof.

In section 6 the vaporous feed thereto which contains numerous varying hydrocarbon components is subjected to severe cracking conditions as aforesaid.

The cracked product leaves section 6 by way of line 7 for further processing, as described above, in the remainder of the olefin plant downstream of the furnace.

Section 3 serves as a trap for entrained liquids that were knocked out of the preheated feed entering zone 4 from line 8. This section provides surface area for contacting with hot gas or gases entering from line 10. The counter current flow within this section 3 device enables the heaviest (highest boiling point) liquids to be contacted at the highest hot gas to oil ratio and with the highest temperature gas at the same time. This creates the most efficient device and operation for vaporization and mild thermal cracking of the heaviest residuum portion of the crude oil feedstock 1 thereby allowing for very high utilization of such crude oil as vaporous feed 5 for severe cracking section 6.

By this invention, such liquids are not just vaporized, but rather are subjected to mild thermal cracking conditions so that lighter molecules are formed from heavier molecules in zone 4 and its associated controlled cavitation device 18 which lighter molecules require less energy for vaporization and removal by way of line 5 for further cracking in section 6.

Thus, in the illustrative embodiment of the Figure, separated liquid hydrocarbon droplets fall downwardly from zone 4 into lower, second zone 9, and are retained or otherwise trapped therein until mild cracking in zone 9 in combination with cavitation conditions in device 18, as explained hereinafter, form vaporous hydrocarbons. These vaporous hydrocarbons make their way into zone 4 and out of section 3 by way of line 5 due to the influence of hot gas 15 rising through zone 9 after being introduced into a lower portion, e.g., bottom, of zone 9 by way of line 10.

In zone 9, a high dilution ratio (hot gas/liquid droplets) is desirable. However, dilution ratios will vary widely because the composition of whole crude oils varies widely. Generally, the hot gas, including multiple gases, to hydrocarbon ratio in section 3 will be from about 0.3/1 to about 5/1, preferably from about 0.3/1 to about 1.2/1, more preferably from about 0.3/1 to about 1/1.

Steam and/or hydrogen are examples of suitable hot gas introduced into zone 9 by way of line 10. Other gases will be obvious to one skilled in the art. Such gases are preferably at a temperature sufficient to volatize and/or mildly crack essentially all, but not necessarily all, of the liquid hydrocarbon that enters zone 9 from zone 4. Generally, the gas entering zone 9 from conduit 10 will be from about 1,000° F. to about 1,300° F. at from about 10 psig to about 30 psig in order to maintain a mild cracking temperature in zone 9 of from about 800° F. to about 1,300° F.

Central portion 12 can contain conventional distillation tower packing, e.g., rings, or other known devices for breaking up and/or distributing falling liquid droplets 14 more uniformly across the lateral, internal cross-section of zone 9. This way, the still liquid droplets that is more difficult to gasify leave central portion 12 and enter bottom portion 13 more finely divided, more evenly distributed, and enjoy good mass transfer when they meet counter current flowing incoming hot gas 15 that is just starting its rise through zone 9 toward zone 4. Thus, these more difficultly vaporized droplets receive the full thermal intensity of the incoming hot gas at its hottest and at a very high ratio of hot gas dilution so that the possibility of thermal cracking and/or vaporizing these tenacious materials is maximized with a minimum of solid residue formation that would remain behind on the high surface area support in that section. This relatively small amount of remaining residue would then be burned off of the support material by conventional steam air decoking. Ideally, this would occur at the same time as the normal furnace decoke cycle common to the prior art cracking process.

The temperature range within section 3, and particularly within zone 9, coupled with the residence time in section 3, particularly zone 9, and the cavitation device 18 should be that which essentially vaporizes most, at least about 90% by weight, if not essentially all, of the remaining liquid whole crude oil feed from line 8. This way essentially all or at least a significant portion of the liquid whole crude primary feed is converted into a gaseous hydrocarbon containing feed for introduction into section 6 by way of conduit 5 for extreme cracking at more elevated temperatures as aforesaid.

In one of the novel aspects of this invention, the aforesaid vaporization of all or essentially all of feed 1 liquids retained in section 3 is provided in part by the use of a controlled cavitation unit 18.

At least part of the heavier liquids that are not yet cracked and/or vaporized that reach bottom portion 13 are removed therefrom by way of line 16 and passed by way line 17 to the input of cavitation unit 18. In unit 18 a myriad of microscopic bubbles are formed in the liquid introduced by way of line 17 which bubbles implode to provide highly localized cracking heat in said liquid and thereby provide additional cracking energy for the more tenacious molecules that resisted vaporization in section 3. Thus, unit 18 provides for the vaporization and/or mild cracking of liquid materials that successfully resisted vaporization and/or mild cracking in their travel through section 3. The liquid and vapor output of unit 18 is removed from unit 18 by way of line 19 and returned to section 3 by way of line 20 for removal of vaporous materials formed in unit 18 to zone 4 and, ultimately, to section 6. Any liquid returned to section 3 by way of line 20 remains trapped in section 3 until ultimately cracked, otherwise vaporized and removed to section 6, or otherwise removed by way of a purge stream described herein after. More than one cavitation device 18 can be used in operable association with liquid from section 3 if desired.

Hydrogen and/or steam can be introduced into bottom portion 13 by way of line 10 for good mixing of same with the liquid hydrocarbon that is resisting vaporization. Such mixing is in and/or around, e.g., above and/or below, packing bed 12. Similarly, steam and/or hydrogen or other gases can be introduced into line 17 by way of line 21 also to assist in the thermal cracking and vaporization of liquid materials to be subjected to controlled cavitation conditions in unit 18. Such steam and/or hydrogen, and the like can be in the same temperature and pressure ranges as in line 10 aforesaid.

Accordingly, unlike conventional prior art cracking processes where the primary hydrocarbon feed transfers from the preheating stage in the convection zone directly to the severe cracking stage in the radiant zone as quickly as possible with little or no cracking between said zones, in accordance with this invention, the liquid hydrocarbon components in the whole crude oil primary feed that are higher boiling and more difficult to gasify are selectively subjected to a combination of increasing intensity vaporization/mild thermal cracking and controlled cavitation conditions for as long as it takes to vaporize a substantial portion, if not all, of said whole crude oil. In this regard, section 3 serves as a trap for liquid hydrocarbons until they are vaporized or cracked until their cracked products are vaporizable and then gasified.

It can be seen that gas from lines 10 and 21 does not serve just as a diluent for partial pressure purposes as does diluent steam introduced, for example, into conduit 1 (not shown). Rather, gas from lines 10 and 21 provides not only a diluting function, but also provides additional vaporizing energy for the hydrocarbons that remain in the liquid state, and further provides mild cracking energy for those hydrocarbons until significant, if not essentially complete, vaporization of desired hydrocarbons is achieved. This is accomplished with just sufficient energy to achieve vaporization of heavier hydrocarbon components, and by controlling the energy input. For example, by using steam in line 10, substantial vaporization of feed 1 liquid is achieved with minimal coke formation in section 3. The very high steam dilution ratio and the highest temperature steam are thereby provided where they are needed most as liquid hydrocarbon droplets move progressively lower in zone 9. In addition, the steam can act to reduce the volume of coke remaining on the catalyst by promoting coke gasification reactions.

Section 3 of the FIG. 1, without unit 18, can be physically contained within the interior of convection zone 2 downstream of the preheating tubes or coils (not shown) so that the mild cracking section 3 of this invention is wholly within the interior of a furnace that contains both convection section 2 and radiant section 6. Unit 18 would be employed outside the furnace but in fluid communication with section 3 inside the furnace. Although total containment of section 3 within a furnace may be desirable for various furnace design considerations, it is not required in order to achieve the benefits of this invention. Section 3 could also be employed wholly or partially outside of the furnace that contains sections 2 and 6 and still be within the spirit of this invention. In this case, preheated feed would leave the interior of the furnace by way of conduit 8 to a location physically wholly or partially outside that furnace. Gaseous feed from physically separate section 3 and its associated unit 18 would then enter conduit 5 and pass by way of such line back into the interior of the furnace and into the interior of section 6. Combinations of the foregoing wholly interior and wholly exterior placement of section 3 with respect to the furnace that contains sections 2 and 6 will be obvious to those skilled in the art and likewise are within the scope of this invention. Generally, any physical means for employing both a mild cracking/vaporizing trap in combination with a controlled cavitation unit between preheating and severe cracking operations, is within this invention.

The operation of mild cracking section 3 of this invention not only can serve as a trap for liquid hydrocarbons until vaporized and/or until mildly cracked and then vaporized, but also can serve as a trap for materials that cannot be cracked or vaporized, whether hydro carbonaceous or not. Typical examples of such materials are metals, inorganic salts, unconverted asphaltenes, and the like. Such materials can be taken from the system by way of a purge stream 22 taken from line 19 or, alternatively from line 17 (not shown).

EXAMPLE

A whole, straight run crude oil stream from a refinery storage tank characterized as Saharan Blend is fed directly into a convection section of a pyrolysis furnace at ambient conditions of temperature and pressure. In this convection section this whole crude oil primary feed is preheated to about 650° F. and then passed into a separate combination mild thermal cracking/controlled cavitation operation wherein gases are separated from liquids, and the gases removed from the mild cracking zone to the radiant section of the same furnace for severe cracking in a temperature range of 1,450° F. to 1,500° F.

The liquid, after separation from accompanying gases, is retained in the mild thermal cracking section 3 and allowed to fall downwardly in that section toward the bottom thereof. Steam at 1,300° F. is introduced into the bottom of zone 9 of section 3 to give a steam to hydrocarbon ratio in zone 9 of 1.2/1. With respect to the liquid falling downwardly in zone 9, the steam to liquid hydrocarbon ratio increases dramatically in section 13 of zone 9 from the top to bottom of zone 9. The falling liquid droplets are in counter current flow with the steam that is rising from the bottom of the section toward the top thereof.

A liquid stream is withdrawn from bottom portion 13 and introduced into a controlled cavitation device described in U.S. Pat. No. 5,492,654 to form a free disperse system in said liquid that contains a plurality of micro bubbles. Such bubbles then implode and generate shock waves that heat various liquid molecules in the location of the bubble implosion to a cracking temperature of from about 800° F. to about 1,300° F. A fluid mixture of liquid materials, cracked liquid materials, and vaporous materials is removed from the cavitation device and returned to zone 9 for further processing. The liquid is retained in zone 9 and caused to encounter additional steam until at least 97% of the hydrocarbons in the primary feed have been either vaporized or mildly cracked and then vaporized.

Reasonable variations and modifications are possible within the scope of this disclosure without departing from the spirit and scope of this invention.

What is claimed is:

1. In a method for operating an olefin production plant that employs a pyrolysis furnace to severely thermally crack hydrocarbon materials for the subsequent processing of said cracked materials in said plant, said furnace having in its interior a convection heating section and a separate radiant heating section, said radiant heating section being employed for said severe cracking, the improvement comprising providing whole crude oil as the primary feedstock to said furnace, preheating said feedstock to a temperature of from about 500° F. to about 750° F. to form a mixture of vaporous and liquid hydrocarbons, collecting said mixture in a vaporization/mild cracking unit, in said unit separating said vaporous hydrocarbons from said liquid hydrocarbons, passing said vaporous hydrocarbons to said radiant heating section, retaining said liquid hydrocarbons in said unit, introducing at least one heated gas into said unit to mix with said liquid hydrocarbons in said unit to dilute said liquid hydrocarbons and heat same to a temperature of from about 800° F. to about 1,300° F. to form additional vaporous hydrocarbons, removing said additional vaporous hydrocarbons to said radiant heating section, removing at least part of said liquid hydrocarbons from said unit and passing same through at least one controlled cavitation device to at least one of vaporize and mildly crack at least part of said removed liquid hydrocarbons thereby forming an additional liquid/vapor mixture in said at least one cavitation device, and returning said additional mixture to said unit.

2. The method of claim 1 wherein said whole crude oil feed is mixed with steam at least one of before and during said preheating.

3. The method of claim 1 wherein said preheating is carried out in said convection heating section.

4. The method of claim 1 wherein essentially all vaporous hydrocarbons are separated from said liquid hydrocarbons so that primarily only hydrocarbon liquid retained in said unit is subjected to both higher heated gas to liquid hydrocarbon ratios and higher heated gas temperatures to cause additional vaporization of said liquid hydrocarbons.

5. The method of claim 1 wherein said heated gas is introduced into said unit at a gas/hydrocarbon dilution ratio of from about 0.3/1 to about 5/1.

6. The method of claim 1 wherein said heated gas is introduced into said unit at a temperature of from about 1,000° F. to about 1,300° F.

7. The method of claim 1 wherein said heated gas is at least one of steam and hydrogen.

8. The method of claim 1 wherein said unit is employed in the interior of said convection heating section, and said device is employed on the exterior of said convection heating section in fluid communication with said unit.

9. The method of claim 1 wherein said unit and said device are both employed outside said furnace but in fluid communication with the interior of said furnace.

10. The method of claim 9 wherein said unit is in fluid communication between said convection heating section and said radiant heating section.

11. The method of claim 1 wherein the retention of liquid hydrocarbons in said unit and said device is continued until a significant portion of said liquid hydrocarbons are converted to vaporous hydrocarbons by at last one of vaporization and mild thermal cracking and removed from said unit and device to said radiant heating section.

12. The method of claim 1 wherein said whole crude oil stream is straight run crude oil that has not been subjected to any distillation, fractionation and the like prior to its introduction into said furnace.

13. The method of claim 4 wherein, in addition to said additional vaporization, at least a portion of said retained liquid hydrocarbons in said unit when encountering said higher gas/liquid hydrocarbon ratios and higher gas temperatures undergoes mild thermal cracking to reduce the molecular weight of at least some of said retained liquid hydrocarbons thereby facilitating the vaporization of same and effecting good utilization of said feed stock as a source of vaporous hydrocarbon feed for said radiant section.

14. The method of claim 1 wherein said device is operated under controlled cavitation conditions such that the liquid in said device is exposed in localized areas to a temperature of at least about 800° F.

15. The method of claim 1 wherein at least one heated gas is introduced into said device to facilitate thermal cracking of liquid therein and enhance vaporization of liquid therein.

16. The method of claim 1 wherein said cavitation device employs a degree of cavitation of at least 0.1.

* * * * *